(12) United States Patent
Schlienger et al.

(10) Patent No.: US 8,313,488 B2
(45) Date of Patent: Nov. 20, 2012

(54) INTRAMEDULLARY NAIL

(75) Inventors: Andre Schlienger, Arlesheim (CH); Markus Buttler, Oensingen (CH); Peter Senn, Waldenburg (CH)

(73) Assignee: Synthes USA, LLC, West Chester, PA (US)

( * ) Notice: Subject to any disclaimer, the term of this patent is extended or adjusted under 35 U.S.C. 154(b) by 617 days.

(21) Appl. No.: 11/450,922

(22) Filed: Jun. 9, 2006

(65) Prior Publication Data
US 2007/0016203 A1  Jan. 18, 2007

Related U.S. Application Data

(63) Continuation of application No. PCT/CH03/00834, filed on Dec. 19, 2003.

(51) Int. Cl.
*A61B 17/72* (2006.01)
(52) U.S. Cl. .......................................... 606/64
(58) Field of Classification Search .............. 606/62–68, 606/98, 329; 623/22.4–23.38
See application file for complete search history.

(56) References Cited

U.S. PATENT DOCUMENTS

| | | | | |
|---|---|---|---|---|
| 4,776,330 A | * | 10/1988 | Chapman et al. | 606/64 |
| 5,021,063 A | * | 6/1991 | Tager | 623/23.33 |
| 5,108,449 A | * | 4/1992 | Gray | 623/23.27 |
| 5,152,794 A | * | 10/1992 | Davidson | 623/23.6 |
| 5,374,235 A | * | 12/1994 | Ahrens | 606/101 |
| 5,429,640 A | * | 7/1995 | Shuler et al. | 606/64 |
| 5,472,444 A |   | 12/1995 | Huebner et al. | |
| 5,971,986 A | * | 10/1999 | Santori et al. | 606/62 |
| 6,010,506 A | * | 1/2000 | Gosney et al. | 606/62 |
| 6,106,528 A | * | 8/2000 | Durham et al. | 606/64 |
| 6,120,504 A | * | 9/2000 | Brumback et al. | 606/62 |
| 6,197,065 B1 | * | 3/2001 | Martin et al. | 623/23.17 |
| 6,322,591 B1 | * | 11/2001 | Ahrens | 623/23.27 |
| 6,447,513 B1 | * | 9/2002 | Griggs | 606/62 |
| 6,454,810 B1 | * | 9/2002 | Lob | 623/23.47 |
| 6,547,791 B1 | * | 4/2003 | Buhren et al. | 606/62 |
| 2002/0099379 A1 | * | 7/2002 | Adam | 606/67 |
| 2002/0151898 A1 | * | 10/2002 | Sohngen et al. | 606/62 |
| 2002/0183750 A1 |   | 12/2002 | Buhler | |
| 2003/0069581 A1 | * | 4/2003 | Stinson et al. | 606/62 |
| 2003/0135211 A1 |   | 7/2003 | Cho | |
| 2003/0135212 A1 |   | 7/2003 | Chow | |

\* cited by examiner

*Primary Examiner* — Alvin Stewart
*Assistant Examiner* — Jerry Cumberledge
(74) *Attorney, Agent, or Firm* — Fay Kaplun & Marcin, LLP

(57) ABSTRACT

The invention relates to an intramedullary nail (1) having a proximal half (2), a distal half (3) adapted for insertion into the medullary canal, and a central axis (4), whereby the distal half (3) includes three transverse bores (5, 6, 7) suitable for receiving locking screws (10). The distal half (3) is provided with a proximal transverse bore (5) having a bore axis (15), a central transverse bore (6) having a bore axis (16), and a distal transverse bore (7) having a bore axis (17) spaced along the central axis (4). The bore axis (16) of the central transverse bore (6), which extends between the proximal transverse bore (5) and the distal transverse bore (7), is spaced at a shortest distance "a" from the bore axis (15) of the proximal transverse bore (5), and at a shortest distance "b" from the bore axis (17) of the distal transverse bore (7), where a≠b.

18 Claims, 3 Drawing Sheets

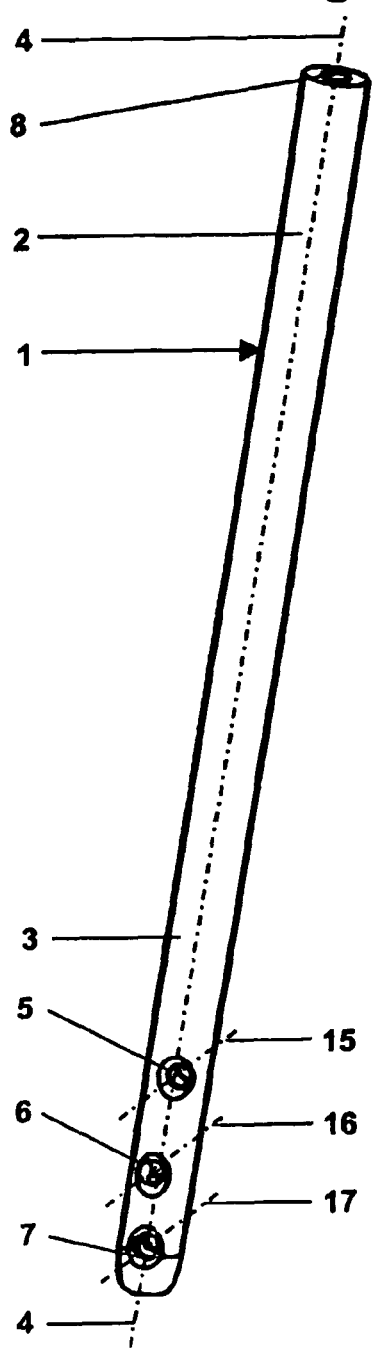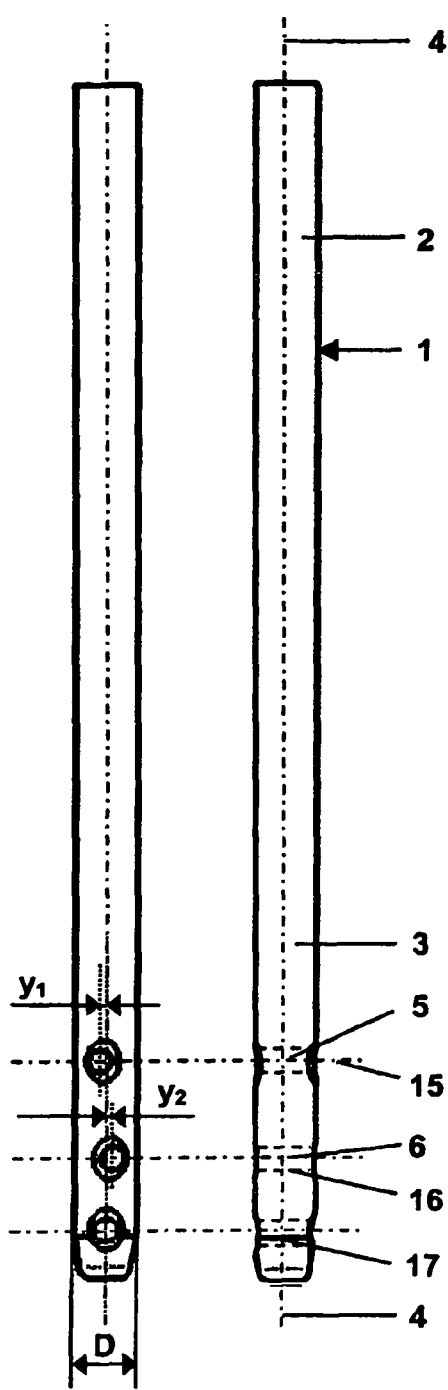

INTRAMEDULLARY NAIL

RELATED APPLICATION DATA

The present application is a continuation of, and claims priority under 35 U.S.C. §120 to, International Patent Application No. PCT/CH2003/000834, filed Dec. 19, 2003, the entire content of which is incorporated herein by reference thereto.

FIELD OF THE INVENTION

The present invention relates to intramedullary nails for use in repairing bone fractures.

BACKGROUND OF THE INVENTION

From FR 1,031,128 to CARRIERI, an intramedullary nail is known which has a plurality of transverse bores, particularly in its distal half. A disadvantage of this known intramedullary nail is the fact that all of the transverse bores are spaced at the same distance from one another and that they are oriented in the same direction. Thus, a central transverse bore lying between two other transverse bores will function as a center of rotation for the connection between a bone fragment and the intramedullary nail, which is undesirable.

The invention is intended to provide a remedy for this. It is accordingly an object of the invention to create an intramedullary nail with a plurality of distal locking bores that is capable, once the distal locking screws have been inserted, of stabilizing the bone fragment held in place by said locking screws and of preventing it from tipping over relative to the nail axis, this being done in a more optimal manner than would be possible with the use of conventional intramedullary nails.

SUMMARY OF THE INVENTION

According to the invention, this object is achieved by means of an intramedullary nail having a nail body with a central longitudinal axis, a proximal portion, and a distal portion adapted for insertion into a medullary canal. At least three transverse bores extend through the distal portion of the nail body suitable for receiving locking screws. The three transverse bores are spaced along the central longitudinal axis and include a proximal transverse bore having a proximal transverse bore axis, a central transverse bore having a central transverse bore axis, and a distal transverse bore having a distal transverse bore axis, wherein the proximal transverse bore is located closer to the proximal portion of the nail body than the distal transverse bore, and the central transverse bore is located between the proximal transverse bore and the distal transverse bore. The central transverse bore axis is spaced a shortest distance "a" from the proximal transverse bore axis and a shortest distance "b" from the distal transverse bore axis, where a≠b. The transverse bore axis of at least one of the three transverse bores may be spaced a non-zero distance yN from the central longitudinal axis of the nail body.

The advantages achieved by the invention reside essentially in the fact that the intramedullary nail according to a preferred embodiment of the present invention, having locking options provided in its distal half, significantly reduces the freedom of the bone fragment, which is held in place by the locking screw, to tip over with respect to the nail axis.

In one particular embodiment of the invention, the bore axis of at least one of the N transverse bores arranged in the distal half is spaced at a distance yN>0 from the central axis. In particular, the bore axis of the central transverse bore may be spaced at a distance y1 >0 and the bore axis of the proximal transverse bore may be spaced at a distance y2>0 from the central axis (4).

In another embodiment the distance "a" is in the range of between 0.6 (a+b) and 0.9 (a+b), and preferably in the range of between 0.7 (a+b) and 0.8 (a+b). The distance "b" may be in the range of between 0.6 (a+b) and 0.9 (a+b), and preferably in the range of between 0.7 (a+b) and 0.8 (a+b).

In a further embodiment, two or more of the transverse bores (5, 6, 7) provided in the distal half (3) intersect one another at least partially.

In a further embodiment, displaying a number N>3 of transverse bores, any sub-combination of three transverse bores may incorporate the features discussed above.

Typically, the sum L=(a+b) is in the range of between 20 mm and 35 mm, preferably in the range of between 24 mm and 30 mm.

In the following, the invention and improvements of the invention will be illustrated in greater detail with reference to the partially diagrammatic representations of several embodiments.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein:

FIG. 4 is a perspective view of an intramedullary nail according to another preferred embodiment of the present invention;

FIG. 5 is a side view of the intramedullary nail of FIG. 4; and

FIG. 6 is a side view of the intramedullary nail of FIG. 4 rotated by 90° with respect to FIG. 5.

monolithic

Figure 7:
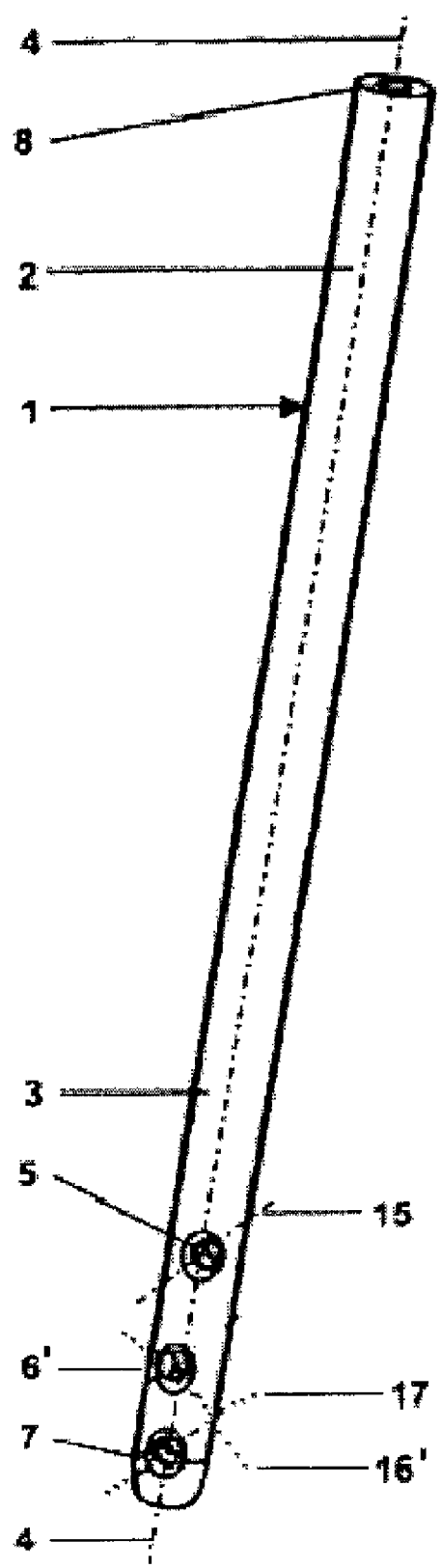

FIG. 7 is a perspective view of an intramedullary nail according to another preferred embodiment of the present invention.

DETAILED DESCRIPTION OF THE PREFERRED EMBODIMENTS

Figure 1:
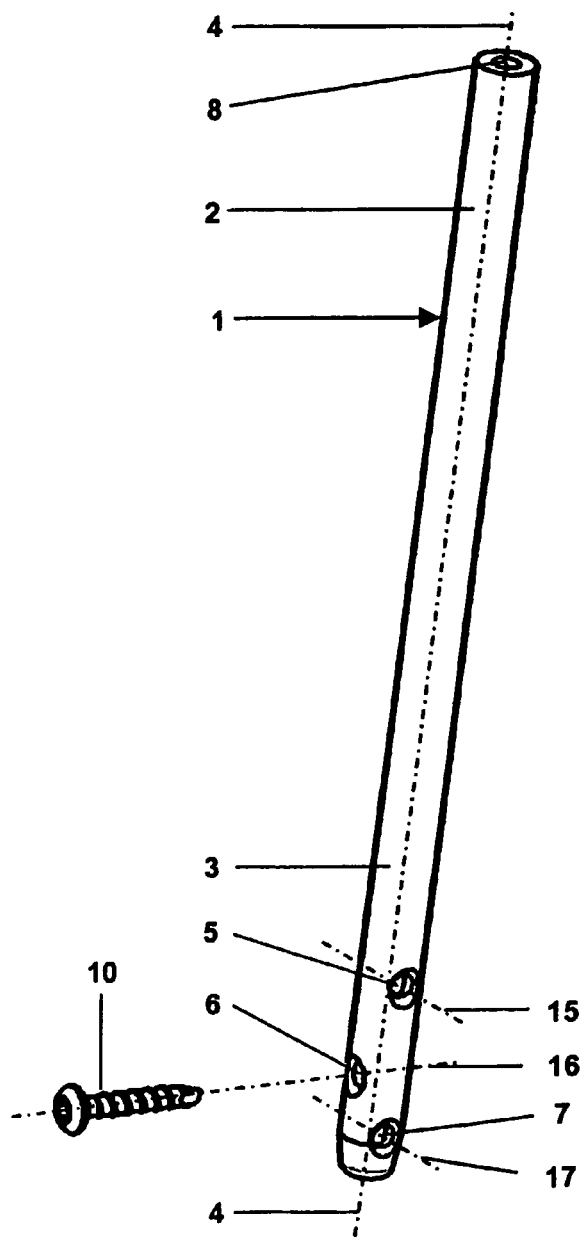
FIG. 1 is a perspective view of an intramedullary nail according to a preferred embodiment of the present invention.
Figure 2:
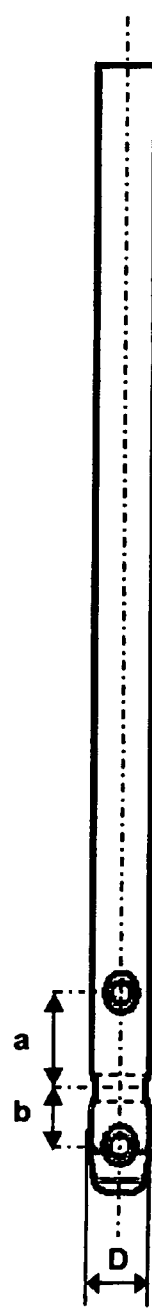
FIG. 2 is a side view of the intramedullary nail of FIG. 1.
Figure 3:
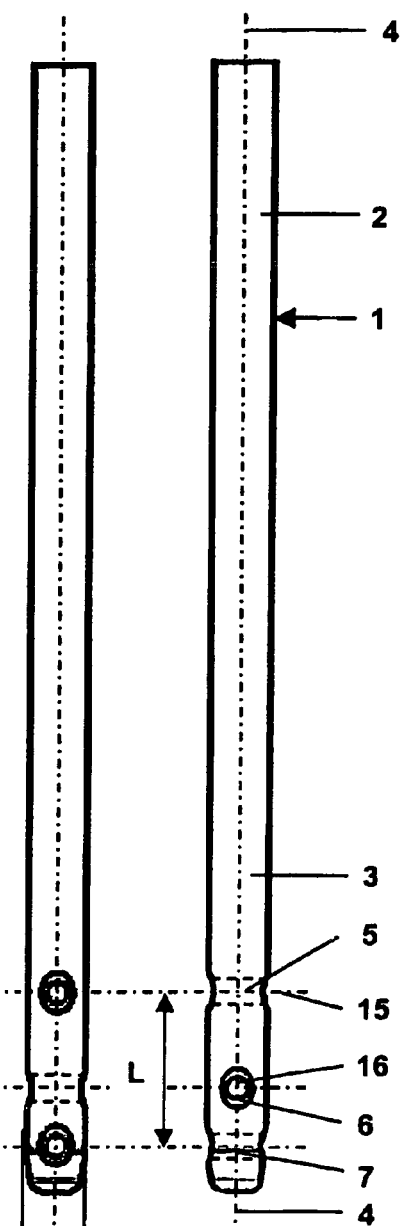
FIG. 3 is a side view of the intramedullary nail of FIG. 1 rotated by 90° with respect to FIG. 2.

The first embodiment of an intramedullary nail 1 as shown in FIGS. 1-3 has a proximal half, a distal half 3 suitable to be inserted into the medullary canal, and a central axis 4. In addition, the intramedullary nail 1 is provided with a cannulation 8 extending over its entire length. The distal half 3 is provided with three transverse bores 5, 6, 7, for the reception of locking screws 10. The proximal transverse bore 5 has a bore axis 15, the central transverse bore 6 a bore axis 16, and the distal transverse bore 7 a bore axis 17. The bore axis 16 of the central transverse bore 6, which extends between the proximal transverse bore 5 and the distal transverse bore 7, is spaced at a shortest distance "a"=16 mm from the bore axis 15 of the proximal transverse bore 5, and at a shortest distance "b"=11 mm from the bore axis 17 of the transverse bore 7. In addition, the condition a≠b is applicable. The sum L=(a+b) is 27 mm. The diameter of the intramedullary nail 1 is D=10 mm.

The second embodiment of an intramedullary nail 1 as shown in FIGS. 4-6 has essentially the same features as the first embodiment, but is provided with the following additional or divergent parameters:

The bore axis 15 of the transverse bore 5 is spaced at a distance y1=0.5 mm from the central axis 4. The bore axis 16 of the transverse bore 6 is equally spaced at a distance y2 =0.5 mm from the central axis 4, but on the opposite side thereof.

A third embodiment of the present invention comprises an intramedullary nail 1 formed substantially similarly as described earlier with the exception of a central transverse bore 6'. Specifically, the central transverse bore 6' extends through the intramedullary nail 1 so that a bore axis 16' thereof intersects with the bore axis 17 of the distal transverse bore 7 at a predetermined depth. The exemplary embodiment of the present invention provides that the bore axes 16' and 17 at least partially intersect one another.

The present invention has been described in connection with the preferred embodiments. Those embodiments, however, are merely for example and the invention is not restricted thereto or limited thereby. Thus, it will be understood by those skilled in the art that other variations and modifications can easily be made within the scope of the invention as defined by the appended claims, and, therefore, the present invention is limited only by the following claims.

What is claimed:

1. An intramedullary nail comprising:
a monolithic nail body having a central longitudinal axis, a proximal portion, and a distal portion adapted for insertion into a medullary canal; and
at least three transverse bores extending through and enclosed within the distal portion of the nail body suitable for receiving locking screws, the three transverse bores spaced along the central longitudinal axis and including a proximal transverse bore having a proximal transverse bore axis, a central transverse bore having a central transverse bore axis, and a distal transverse bore having a distal transverse bore axis,
wherein the proximal transverse bore is located closer to the proximal portion of the nail body than the distal transverse bore, and the central transverse bore is located between the proximal transverse bore and the distal transverse bore,
wherein the central transverse bore axis is spaced a shortest distance "a" from the proximal transverse bore axis and a shortest distance "b" from the distal transverse bore axis, where a≠b, and the transverse bore axis of at least one of the three transverse bores is spaced a non-zero distance yN from the central longitudinal axis of the nail body.

2. The intramedullary nail of claim 1, wherein the central transverse bore axis is spaced a non-zero distance y1 from the central longitudinal axis.

3. The intramedullary nail of claim 1, wherein the proximal transverse bore axis is spaced a non-zero distance y2 from the central longitudinal axis.

4. The intramedullary nail of claim 1, wherein "a" is in the range of between 0.6 (a+b) and 0.9 (a+b).

5. The intramedullary nail of claim 4, wherein "a" is in the range of between 0.7 (a+b) and 0.8 (a+b).

6. The intramedullary nail of claim 1, wherein "b" is in the range of between 0.6 (a+b) and 0.9 (a+b).

7. The intramedullary nail of claim 6, wherein "b" is in the range of between 0.7 (a+b) and 0.8 (a+b).

8. The intramedullary nail of claim 1, wherein at least two of the transverse bores at least partially intersect one another.

9. The intramedullary nail of claim 1, wherein the total distance L=(a+b) between the proximal transverse bore axis and the distal transverse bore axis is in the range of between 20 mm and 35 mm.

10. The intramedullary nail of claim 9, wherein the distance L=(a+b) is in the range of between 24 mm and 30 mm.

11. The intramedullary nail of claim 1, wherein the nail body includes a lengthwise cannulation extending coaxially with the central longitudinal axis.

12. The intramedullary nail of claim 1, wherein the proximal transverse bore axis and the central transverse bore axis are parallel.

13. The intramedullary nail of claim 1, wherein the proximal transverse bore axis and the central transverse bore axis are substantially perpendicular to the central longitudinal axis of the nail body.

14. The intramedullary nail of claim 13, wherein the proximal transverse bore axis and the central transverse bore axis intersect to form a non-zero angle when projected into a plane substantially perpendicular to the central longitudinal axis of the nail body.

15. An intramedullary nail for use in repairing bone fractures comprising:
a nail body having a central longitudinal axis, a proximal portion, and a distal portion including a taper and adapted for insertion into a medullary canal of a fractured bone; and
at least three transverse bores extending through and enclosed within the distal portion of the nail body adapted for receiving locking screws, the at least three transverse bores including a proximal bore closest to the proximal portion of the nail body, a distal bore, and a central bore disposed between the proximal and distal bores,
wherein the at least three transverse bores are unequally spaced along the central longitudinal axis such that the distance between the central bore and the proximal bore , does not equal the distance between the central bore and the distal bore, and at least one of the transverse bores having a transverse bore axis offset a non-zero distance from the central longitudinal axis of the nail body.

16. The intramedullary nail of claim 15, wherein the proximal bore and the central bore have transverse axes that are substantially parallel to one another.

17. The intramedullary nail of claim 15, wherein the proximal bore and the central bore have transverse axes that are substantially perpendicular to the central longitudinal axis of the nail body.

18. The intramedullary nail of claim 17, wherein the transverse axes of the proximal bore and central bore intersect to form a non-zero angle when projected onto a plane substantially perpendicular to the central longitudinal axis of the nail body.

* * * * *